US011214838B2

(12) United States Patent
Mukai et al.

(10) Patent No.: US 11,214,838 B2
(45) Date of Patent: Jan. 4, 2022

(54) METHOD OF PREDICTING EFFECT OF MEDICINAL THERAPY ON CANCER

(71) Applicants: NATIONAL CANCER CENTER, Chuo-ku (JP); H.U. Group Research Institute G.K., Hachioji (JP)

(72) Inventors: Hirofumi Mukai, Chiba (JP); Toshikazu Ushijima, Tokyo (JP); Satoshi Yamashita, Tokyo (JP)

(73) Assignees: NATIONAL CANCER CENTER, Chuo-ku (JP); H.U. Group Research Institute G.K., Hachioji (JP)

( * ) Notice: Subject to any disclaimer, the term of this patent is extended or adjusted under 35 U.S.C. 154(b) by 0 days.

(21) Appl. No.: 16/308,210

(22) PCT Filed: Mar. 15, 2017

(86) PCT No.: PCT/JP2017/010523
§ 371 (c)(1),
(2) Date: Dec. 7, 2018

(87) PCT Pub. No.: WO2017/212734
PCT Pub. Date: Dec. 14, 2017

(65) Prior Publication Data
US 2019/0169701 A1 Jun. 6, 2019

(30) Foreign Application Priority Data
Jun. 10, 2016 (JP) .............................. JP2016-116367

(51) Int. Cl.
| | | |
|---|---|---|
| *C12Q 1/68* | (2018.01) | |
| *C12Q 1/6886* | (2018.01) | |
| *A61P 35/00* | (2006.01) | |
| *A61K 45/00* | (2006.01) | |
| *A61K 39/395* | (2006.01) | |
| *G01N 33/53* | (2006.01) | |
| *G01N 33/574* | (2006.01) | |

(52) U.S. Cl.
CPC .......... *C12Q 1/6886* (2013.01); *A61K 39/395* (2013.01); *A61K 45/00* (2013.01); *A61P 35/00* (2018.01); *C12Q 1/68* (2013.01); *G01N 33/53* (2013.01); *G01N 33/574* (2013.01); *G01N 33/57415* (2013.01); *C12Q 2600/154* (2013.01)

(58) Field of Classification Search
None
See application file for complete search history.

(56) References Cited

U.S. PATENT DOCUMENTS 10,316,361 B2 * 6/2019 Sukumar ............... C12Q 1/6886
2009/0162836 A1 6/2009 Widschwendter

FOREIGN PATENT DOCUMENTS

WO WO 2005/040421 A2 5/2005

OTHER PUBLICATIONS

Widschwendter et al. (Cancer Research 64, 3807-3813, Jun. 1, 2004) (Year: 2004).*
Fackler MJ, McVeigh M, Mehrotra J, Blum MA, Lange J, Lapides A, et al. Quantitative multiplex methylation-specific PCR assay for the detection of promoter hypermethylation in multiple genes in breast cancer. Cancer Res 2004;64:4442-52. (Year: 2004).*
Fackler et al. Genome-wide Methylation Analysis Identifies Genes Specific to Breast Cancer Hormone Receptor Status and Risk of Recurrence.Cancer Res;2011: 71(19); 6195-6207. (Year: 2011).*
Verma and Manne. Genetic and epigenetic biomarkers in cancer diagnosis and identifying high risk populations. Critical Reviews in Oncology/Hematology 60 (2006) 9-18. (Year: 2006).*
Fiegl et al. Breast Cancer DNA Methylation Profiles in Cancer Cells and Tumor Stroma: Association with HER-2/neu Status in Primary Breast Cancer. Cancer Res; 2006; 66: (1): 29-33. (Year: 2006).*
Nahta and Esteva. HER2 therapy Molecular mechanisms of trastuzumab resistance.Breast Cancer Research 2006, 8:215 (doi: 10.1186/bcr1612). (Year: 2006).*
Lindqvist et al. Whole genome DNA methylation signature of HER2-positive breast cancer. Epigenetics, 2014 9:8, 1149-1162. (Year: 2014).*
Fujii et al. Pathological complete response of HER2-positive breast cancer to trastuzumab and chemotherapy can be predicted by HSD17B4 methylation. Oncotarget, Feb. 6, 2017, vol. 8, (No. 12), pp. 19039-19048 (Year: 2017).*
Hackenberg et al. Prediction of CpG-island function: CpG clustering vs. sliding-window methods. BMC Genomics; 2010;11:327:1-14. (Year: 2010).*
Chen et al. Identifying Methylation Pattern and Genes Associated with Breast Cancer Subtypes. Int. J. Mol. Sci.; 2019; 20; 4269: p. 1-20. (Year: 2019).*
Pernas and Tolaney. HER2-positive breast cancer: new therapeutic frontiers and overcoming. Ther Adv Med Oncol; 2019; vol. 11: 1-16. (Year: 2019).*
Extended European Search Report dated Nov. 27, 2019 in Patent Application No. 17809918.0, citing document AX therein, 9 pages.
Hosny, M.M. et al. "Promoter Methylation Status of Breast Cancer Susceptibility Gene 1 and 17 Beta Hydroxysteroid Dehydrogenase Type 1 Gene in Sporadic Breast Cancer Patients" International Journal of Breast Cancer, vol. 2016, XP002795118, 2016, 13 pages.

(Continued)

*Primary Examiner* — Juliet C Switzer
*Assistant Examiner* — Wahwah T Johnson
(74) *Attorney, Agent, or Firm* — Oblon, McClelland, Maier & Neustadt, L.L.P.

(57) ABSTRACT

The present invention provides a factor capable of predicting an effect of a medicinal therapy on a cancer such as HER2 positive cancer. More specifically, the present invention provides a method of predicting the effect of the medicinal therapy on the cancer, comprising:
(1) analyzing a methylation level of a cytosine residue in one or more CpG sites present within a nucleotide sequence in a promotor region, an untranslated region or a translated region of HSD17B4 gene in a sample taken from a human subject; and
(2) predicting the effect of the medicinal therapy on the cancer based on the analyzed methylation level.

9 Claims, 3 Drawing Sheets
Specification includes a Sequence Listing.

(56) References Cited

OTHER PUBLICATIONS

International Search Report dated May 30, 2017 in PCT/JP2017/010523 Filed on Mar. 15, 2017.
Fiegl, H. et al. "Breast Cancer DNA Methylation Profiles in Cancer Celis and Tumor Stroma: Association with HER-2/neu Status in Primary Breast Cancer", Cancer Research, 2006, vol. 66, No. 1, pp. 29-33.
Fujii, S. et al. "Pathological complete response of HER2-positive breast cancer to trastuzumab and chemotherapy can be predicted by HSD17B4 methylation", Oncotarget, Feb. 6, 2017, vol. 8, No. 12, pp. 19039-19048.
Yamaguchi, T., et al. "Comprehensive DNA Methylation and Extensive Mutation Analyses of HER2-Positive Breast Cancer", Oncology, 2015, pp. 377-384.
European Office Action dated Jul. 8, 2020 in European Patent Application No. 17809918.0, citing document AX therein, 9 pages.
Anonymous, "Infinium® HumanMethylation450 BeadChip," Illumina, Inc., Retrieved from the Internet [URL: https://support.illumina.com/content/dam/illumina-marketing/documents/products/datasheets/datasheet_humanmethylation450.pdf], XP055401052, Mar. 9, 2012, 4 pages.

* cited by examiner

FIG. 1

HSD17B4

```
    -10              1                                  20
     cgcgctctgcgctcatcttcctaccagaaatcggcaagtc
                   ↳
                                              60
     actgacctcgtcccgccccgccattccccgcctcctcc
                                    cg15896301 target        #5
                                              ↓       100
     tgtcccgcagtcggcgtccagcggctctgcttgtcgtgt
          #4        #3   #2          #1          (SEQ ID NO:1)
     Sequence to read (pyrosequencing)
```

METHOD OF PREDICTING EFFECT OF MEDICINAL THERAPY ON CANCER

TECHNICAL FIELD

The present invention relates to a method of predicting an effect of a medicinal therapy on a cancer.

BACKGROUND ART

Conventionally, medicinal therapies, surgical operations, and the like have been performed as therapies on cancers. For example, in the guideline from the Japanese Breast Cancer Society, it has been recommended that the surgical operation is performed as a general rule for all cases of treatments of patients with breast cancer having no distant metastasis. However, the surgical operation, particularly a breast removal operation highly potentially leads to cure of breast cancer, but the patient greatly suffers from breast loss. Thus, it has been discussed whether it is necessary or not to apply the surgical operation to all cases, even to the case in which a good response has been obtained by a neoadjuvant medicinal therapy.

Meanwhile, for example, the presence or absence or the change in dose of the expression of a particular gene or protein, the presence or absence or the change in dose of a particular metabolite, and the presence or absence or the degree of a genetic polymorphism (e.g., SNP, haplotype), a translocation, or the methylation of genomic DNA are known as factors of diseases such as cancers (e.g., diagnosis markers, markers for evaluation of disease risk). As such a factor, for example, genomic DNA methylation was analyzed in HER2-positive breast cancer, and multiple methylation sites capable of being associated with behavior of the HER2-positive breast cancer have been found (Non-patent Literature 1).

PRIOR ART REFERENCES

Non-Patent Literatures

Non-patent Literature 1: Oncology, 2015; 88: pp. 377-384.

SUMMARY OF INVENTION

Problem to be Solved by the Invention

However, no factor capable of predicting a case that is curable with a neoadjuvant medicinal therapy has been revealed among cancer cases such as HER2-positive cancers.

It is an object of the present invention to provide a factor capable of predicting an effect of a medicinal therapy on cancers such as HER2-positive cancers.

Means for Solving Problem

As a result of an extensive study, the present inventors have found that a methylation level of a particular CpG site in a non-coding region of HSD17B4 gene can be utilized as a factor capable of predicting an effect of a medicinal therapy on cancers, and have completed the present invention.

That is, the present inventions are as follows.

[1] A method of predicting an effect of a medicinal therapy on a cancer, comprising:
(1) analyzing a methylation level of a cytosine residue in one or more CpG sites present within a nucleotide sequence in a promotor region, an untranslated region or a translated region of HSD17B4 gene in a sample taken from a human subject; and
(2) predicting the effect of the medicinal therapy on the cancer based on the analyzed methylation level.

[2] The method described in [1], wherein the sample taken from the human subject is one or two or more samples selected from the group consisting of a blood, a body fluid, a tissue, and a cell.

[3] The method described in [1] or [2], wherein the CpG site is a CpG site normally present between positions 56 and 94 on the basis of a transcription start site.

[4] The method described in [3], wherein the CpG site is a CpG site normally present at positions 92 and 93 on the basis of the transcription start site.

[5] The method described in any one of [1] to [4], wherein the cancer is a HER2-positive cancer.

[6] The method described in any one of [1] to [5], wherein the cancer is a breast cancer.

[7] The method described in [6], further comprising measuring the expression of estrogen receptor in the sample.

[8] The method described in any one of [1] to [7], wherein the medicinal therapy is a treatment with a HER2 inhibitor.

[9] The method described in [8], wherein the HER2 inhibitor is an antibody.

[10] The method described in [9], wherein the antibody is trastuzumab.

[11] The method described in any one of [1] to [10], wherein the analysis is performed using one or two or more means selected from the group consisting of bisulfite, one or more primers, one or more nucleic acid probes, a restriction enzyme, an anti-methylated cytosine antibody, and a nanopore.

[12] The method described in any one of [1] to [11], wherein the analysis is performed by a bisulfite sequencing method, a bisulfite pyrosequencing method, a methylation specific PCR method, a restriction enzyme landmark genome scanning (RLGS) method, a single nucleotide primer extension (SNuPE) method, a CpG island microarray method, a MethyLight method, a COBRA method, a mass spectroscopy (mass array) method, use of a methylation specific restriction enzyme, a high resolution melting analysis (HRM) method, a nanopore analysis method, an ICON probe method, a methylation specific MLPA method, or an immunoassay.

[13] A diagnosis kit for an effect of a medicinal therapy on a cancer, comprising an analytical means for analyzing methylation of a cytosine residue in one or more CpG sites present within a nucleotide sequence in a promotor region, an untranslated region or a translated region of HSD17B4 gene.

[14] The diagnosis kit described in [13], wherein the CpG site is a CpG site normally present between positions 56 and 94 on the basis of a transcription start site.

[15] The diagnosis kit described in [14], wherein the CpG site is a CpG site normally present at positions 92 and 93 on the basis of the transcription start site.

[16] The diagnosis kit described in any one of [13] to [15], wherein the analytical means is one or two or more means selected from the group consisting of bisulfite, one or more primers, one or more nucleic acid probes, a restriction enzyme, an anti-methylated cytosine antibody, and a nanopore.

[17] A medicinal therapy on a cancer, comprising:
(1) analyzing a methylation level of a cytosine residue in one or more CpG sites present within a nucleotide sequence in a promotor region, an untranslated region or a translated region of HSD17B4 gene in a sample taken from a human subject; and
(2) predicting an effect of the medicinal therapy on the cancer based on the analyzed methylation level; and
(3) selecting a human predicted to receive the effect of the medicinal therapy on the cancer; and
(4) giving the medicinal therapy to the selected human.

[18] A method of selecting a treatment on a cancer, comprising:
(1) analyzing a methylation level of a cytosine residue in one or more CpG sites present within a nucleotide sequence in a promotor region, an untranslated region or a translated region of HSD17B4 gene in a sample taken from a human subject; and
(2) selecting the treatment on the cancer based on the analyzed methylation level.

Effect of the Invention

The prediction method of the present invention is, for example, useful as the factor for determining whether the surgical operation is required or not for the patient with the cancer such as HER2-positive cancer and in judgement of selection of the medicinal therapy.

The kit of the present invention is, for example, useful for simply performing the prediction method of the present invention.

The medicinal therapy of the present invention is useful for the effective treatment with an anticancer agent.

EMBODIMENTS FOR CARRYING OUT THE INVENTION

The present invention provides a method of predicting an effect of a medicinal therapy on a cancer.

The cancer is any cancer. Examples of the cancer include breast cancer (e.g., invasive ductal carcinoma, invasive lobular carcinoma), ovarian cancer, uterus cancer (e.g., endometrial cancer, cervical cancer), lung cancer (e.g., non-small cell cancer such as squamous cancer, adenocarcinoma and large cell cancer, and small cell cancer), gastrointestinal cancer (e.g., stomach cancer, small intestine cancer, large intestine cancer, rectal cancer), pancreatic cancer, renal cancer, hepatic cancer, thymus cancer, spleen cancer, thyroid gland cancer, adrenal cancer, prostate cancer, urinary bladder cancer, bone cancer, skin cancer, cerebral tumor, sarcoma, melanoma, blastoma (e.g., neuroblastoma), adenocarcinoma, squamous cell carcinoma, solid carcinoma, epithelial cancer, and mesothelioma, and breast cancer is preferred. Also examples of the cancer include HER2-positive cancer, EGFR-positive cancer, c-MET-positive cancer, ALK-positive cancer, PGDFR-positive cancer, and c-KIT-positive cancer, and HER2-positive cancer is preferred. In particular, the cancer is preferably HER2-positive breast cancer.

Examples of the medicinal therapy on the cancer include treatments with an anticancer agent. Examples of the anticancer agent include microtubule inhibitors, anticancer antibiotics, topoisomerase inhibitors, platinum formulations, and alkylating agents. The anticancer agent may be a molecular targeted drug. Examples of such a molecular targeted drug include HER2 inhibitors, EGFR inhibitors (e.g., gefitinib, lapatinib, erlotinib, cetuximab), c-MET inhibitors (e.g., PHA-665752, SU11274, XL-880), ALK inhibitors (e.g., WHI-P154, TAE684, PF-2341066), PDGFR inhibitors (e.g., imatinib, desatinib, valatinib), and c-KIT inhibitors (e.g., sunitinib, masitinib, motesanib).

Preferably, the medicinal therapy on the cancer is a treatment with the HER2 inhibitor. HER2 is receptor type tyrosine kinase belonging to the same family as epithelial growth factor (EGFR). HER2 has a structure in which an extracellular domain, a transmembrane domain and an intracellular domain having tyrosine kinase activity are linked on a single strand (see e.g., Coussens et al., Science, 985, Vol. 230, No. 4730, pp. 1132-1139, and GenBank accession number: NP_001005862.1). Examples of the HER2 inhibitor include antibodies (e.g., trastuzumab, pertuzumab), low molecular organic compounds (e.g., HER2 tyrosine kinase inhibitors such as lapatinib, neratinib, afatinib), and drug-conjugated antibodies (e.g., T-DM1).

In the medicinal therapy on the cancer, a plurality of anticancer agents can be used in combination. The combination of a plurality of anticancer agents includes, for example, a combination of two or more aforementioned anticancer agents, and a combination of one or more aforementioned anticancer agents with other anticancer agents. Examples of the other anticancer agents include microtubule inhibitors such as taxane-based anticancer agents (e.g., paclitaxel), anthracycline-based anticancer agents (e.g., ADRIACIN), and aromatase inhibitors (e.g., letrozole).

The medicinal therapy on the cancer includes uses of pharmaceuticals capable of suppressing or promoting the expression of HSD17B4 gene, particularly pharmaceuticals capable of suppressing the expression, and pharmaceuticals capable of methylating, particularly, a non-coding region of HSD17B4 gene, in addition to uses of the known anticancer agents described above.

The method of the present invention comprises the following (1) and (2)
(1) analyzing a methylation level of a cytosine residue in one or more CpG sites present within a nucleotide sequence in a promotor region, an untranslated region or a translated region of HSD17B4 gene in a sample taken from a human subject; and
(2) predicting an effect of the medicinal therapy on the cancer based on the analyzed methylation level.

In step (1), as the samples, one or two or more samples selected from the group consisting of blood, body fluid, tissue and a cell can be used and a tissue sample corresponding to the aforementioned cancer can be suitably used. In the present invention, in a genomic DNA contained in such a cancer tissue sample, a specific CpG site is analyzed.

The genomic DNA can be extracted as appropriate from the cancer tissue sample. As the cancer tissue sample, those collected by biopsy such as core needle biopsy can be used. The cancer tissue sample may be subjected to a pretreatment. Such a pretreatment includes, for example, extraction, cell fixation, tissue fixation, tissue slicing, cell dissociation treatment, heating, freezing, cold storage, and liquefaction.

The cancer tissue sample is typically a sample of a cell population comprising cancer cells and normal cells (non-cancer cells). Therefore, in order to actually measure the methylation level of genomic DNA in a pure cancer cell population, the cancer cell population may be sorted out and collected from the cancer tissue sample. An example of a preferred method which enables such collection is laser microdissection (LMD) method. According to LMD method, the cancer cell population contained in a tissue section can be collected by dissection with laser (e.g., infrared laser, ultraviolet laser). LMD method can be carried out, for example, by using an apparatus such as LMD6500/7000 (Leica), PALM MicroBeam (ZEISS). The other method which enables such a collection includes, for example, any method (e.g., FACS) which can sort out the cancer cell utilizing a cancer cell marker (e.g., protein marker) and, as needed, a label (e.g., fluorescent label).

The CpG site to be analyzed in the present invention is one or more CpG sites present within a nucleotide sequence in a promotor region, an untranslated region or a translated region of HSD17B4 gene. In particular, the CpG site normally present between positions 56 and 94 on the basis of the transcription start site is preferable, and the CpG site normally present at positions 92 and 93 on the basis of the transcription start site of HSD17B4 gene is more preferable (see cg15896301 in FIG. 1). In the present specification, the "transcription start site" is meant to be determined based on GRCh37 (Genome Reference Consortium human build 37) and Hg19 (UCSC human genome 19). Such a CpG site is present at a location of nucleotide residues at positions 102 and 103 in the nucleotide sequence of SEQ ID NO:1 shown in FIG. 1 (nucleotide sequence starting from a nucleotide residue at position −10 from the transcription start site), and is present at a location of nucleotide residues at positions 1092 and 1093 in the nucleotide sequence of SEQ ID NO:2 that describes a surrounding nucleotide sequence of the transcription start site in HSD17B4 gene. Of course, a mutation in genomic DNA (e.g., deletion, insertion, substitution of DNA) may be present between human subjects, and thus, the above location and the nucleotide sequences of the above SEQ ID NOs may vary. For example, when SNP (single nucleotide polymorphism) that is one nucleotide residue insertion or deletion is present between the transcription start site in HSD17B4 gene and the above CpG site, the above location is shifted by one. Also when a mutation is present in genomic DNA, the nucleotide sequence of the above SEQ ID NO varies. Therefore, the above location and the nucleotide sequence of the above SEQ ID NO are "standard" ones for convenience in reference. Alternatively, the CpG site to be analyzed in the present invention can be also defined as a CG portion in cagcggct (e.g., nucleotide residues at positions 99 to 106 in the nucleotide sequence of SEQ ID NO:1, or nucleotide residues at positions 1089 to 1096 in the nucleotide sequence of SEQ ID NO:2) present within the non-coding region downstream of the transcription start site in HSD17B4 gene (when the cag portion on the 5' side and the get portion on the 3' side are not mutated). A person skilled in the art can appropriately determine the CpG site corresponding to the CpG site present at the above location by considering the mutation in the genomic DNA for the human subject having the mutation in the genomic DNA.

The methylation to be analyzed in the present invention is the methylation at position 5 in the cytosine residue.

Analysis of the methylation level can be performed by any method known in the art. For example, the analysis can be performed using one or two or more analytical means selected from the group consisting of bisulfite, one or more primers, one or more nucleic acid probes, a restriction enzyme, an anti-methylated cytosine antibody, and a nanopore.

Bisulfite converts non-methylated cytosine to uracil whereas it does not convert methylated cytosine to uracil. Thus, due to such nature, bisulfite is commonly used for analysis of methylated cytosine in combination of other analytical means.

The one or more primers (e.g., one to three primers) are primers for sequencing or primers for gene amplification (e.g., PCR primers) or a combination thereof. The primer can be appropriately designed so as to analyze an objective CpG site. For example, the primer can be designed to anneal to a downstream region of the objective CpG site (e.g., any region within the portion consisting of nucleotide residues at positions 1094 to 2001 in the nucleotide sequence of SEQ ID NO:2), or can be designed so that a sense strand and an antisense strand are annealed in an upstream region of the objective CpG site (e.g., any region within the portion consisting of nucleotide residues at positions 1 to 1091 in the nucleotide sequence of SEQ ID NO:2) and a downstream region of the objective CpG site (e.g., any region within the portion consisting of nucleotide residues at positions 1094 to 2001 in the nucleotide sequence of SEQ ID NO:2) in order to amplify a gene region including the objective CpG site.

The one or more nucleic acid probes (e.g., one to three nucleic acid probes) can be designed to hybridize with a region including the objective CpG site (portion including the objective CpG site within the portion consisting of nucleotide residues at positions 1 to 120 in the nucleotide sequence of SEQ ID NO:1), or an upstream region thereof (e.g., any region within the portion consisting of nucleotide residues at positions 1 to 1091 in the nucleotide sequence of SEQ ID NO:2), or a downstream region thereof (e.g., any region within the portion consisting of nucleotide residues at positions 1094 to 2001 in the nucleotide sequence of SEQ ID NO:2). The nucleic acid probe can be used in a free form or in a form immobilized to a solid phase. Examples of the solid phase include particles (e.g., magnetic particles); supports such as array, membrane (e.g., nitrocellulose membrane, filter), columns; and containers such as plates (e.g., multiwell plates) and tubes. Materials for the solid phase include, for example, glasses, plastics, and metals. The nucleic acid probe may be the nucleic acid probe described in detail in the analysis of methylated cytosine using the anti-methylated cytosine antibody.

The restriction enzyme is a methylation-specific or -non-specific restriction enzyme, and can be used appropriately in combination with the bisulfite, the one or more primers, or the one or more nucleic acid probes as described above.

Specifically, analytical methods using the analytical means as described above include, for example, a bisulfite sequencing method, a bisulfite pyrosequencing method, a methylation specific PCR method, a restriction enzyme landmark genome scanning (RLGS) method, a single nucleotide primer extension (SNuPE) method, a CpG island microarray method, a MethyLight method, a COBRA method, a mass spectroscopy (mass array) method, use of a methylation specific restriction enzyme, a high resolution melting analysis (HRM) method, a nanopore analysis method, an ICON probe method, and a methylation specific MLPA method. These methods are well-known in the art (e.g., Japanese Patent Application Publication No. 2012-090555, No. 2014-036672, Japanese Patent Application Publication No. 2010-538638, Domestic re-publication of WO 2009/136501).

The analysis can be also performed using an anti-methylated cytosine antibody. The analysis of methylated cytosine using the anti-methylated cytosine antibody is well-known in the art (e.g., WO2015/025862; WO2015/025863; WO2015/025864; WO2016/052368; Japanese Patent Application Publication No. 2012-230019; DNA Research 13, 37-42 (2006); Anal. Chem. 2012, 84, 7533-7538). The anti-methylated cytosine antibody may be used in combination with one or two or more analytical means as described above. Specifically, methods using such analytical means include, for example, a method of using the anti-methylated cytosine antibody and heterogeneous nucleic acid probes in combination (e.g., normal RNA probes, modified RNA probes) (e.g., WO2015/025862); a method of using the anti-methylated cytosine antibody and a solid phase probe and a capture probe in combination (e.g., WO2015/025863); a method of using the anti-methylated cytosine antibody and an absorbent polynucleotide and a capture probe in combination (e.g., WO2015/025864); and a method of using the anti-methylated cytosine antibody and a modified nucleobase paired heterogeneous nucleic acid probe in combination (e.g., WO2016/052368). The nucleic acid probe used in combination with the anti-methylated cytosine antibody may be designed so that a methylcytosine residue in the CpG site forms a portion unpaired with the nucleic acid probe (in other words, not bound in a complementary manner) when the nucleic acid probe is hybridized with a DNA strand including the above CpG site to be analyzed in the present invention to form a double strand structure consisting of the DNA strand and the nucleic acid probe (e.g., WO2015/025862). Therefore, the nucleic acid probe may have a nucleotide residue (e.g., cytosine residue, thymine residue, adenine residue, uracil residue) other than a guanine residue that can bind complementarily to the methylcytosine residue as a nucleotide residue corresponding to the unpaired portion. Alternatively, the nucleic acid probe may be designed so that such an unpaired portion is not formed (WO2016/052368).

The method of using the anti-methylated cytosine antibody can be performed by any immunological method known in the art. Specifically, examples of such a method include an enzyme immunoassay (EIA) (e.g., CLEIA, ELISA), a fluorescent immunoassay, a chemiluminescent immunoassay, electrochemical luminescent immunoassay, an aggregation method, immunostaining, a flow cytometry method, a biolayer interferometry method, an In Situ PLA method, a chemical amplification type luminescence proximity homogeneous assay, a line blot method, and a western blot method.

The methylation level to be analyzed in the present invention is a ratio of the methylation of the cytosine residue in the above CpG in the cancer cells. Measurement of the methylation level is well-known in the art (e.g., Japanese Patent Application Publication No. 2012-090555, Japanese Patent Application Publication No. 2014-036672, Japanese Patent Application Publication No. 2010-538638, Domestic re-publication of WO 2009/136501).

In one embodiment, the methylation level is analyzed without sorting out cancer cells from the cancer tissue sample. The cancer tissue sample typically includes cancer cells and normal cells. When the methylation level is analyzed in such a cancer tissue sample, the methylation level in the cancer cells can be calculated by correcting an actually measured methylation level with a cancer cell ratio [cancer cells/(cancer cells+normal cells)]. The cancer cell ratio in the cancer tissue sample can be obtained by any method in the art. For example, the cancer cell ratio can be obtained by microscopic examination or a method using a cancer cell marker and/or a normal cell marker (e.g., a protein marker) and a label (e.g., fluorescent label). Alternatively, when the methylation level is analyzed in such a cancer tissue sample, the methylation level may further be corrected by considering a normal cell existence ratio [normal cells/(cancer cells+normal cells)] in the cancer tissue sample and the methylation level in the normal cells.

In another embodiment, the methylation level is analyzed after sorting out cancer cells from the cancer tissue sample. In this case, the actually measured methylation level may directly be used as the methylation level. Sorting out cancer cells from the cancer tissue sample can be performed by the method as described above.

In step (2), the effect of the medicinal therapy on the cancer is predicted based on the analyzed methylation level. The analyzed methylation level is used as a factor for comparing with a standard value. The methylation level of the above CpG site is significantly high in a subject group in which the medicinal therapy on the cancer is effective (effective group) compared with a subject group in which the medicinal therapy on the cancer is not effective (ineffective group). Therefore, according to the present invention, when the methylation level of the above CpG site is equal to or higher than the standard value, it can be predicted that a subject has a high possibility that the medicinal therapy on the cancer is effective, and/or a low possibility that the medicinal therapy on the cancer is not effective. In addition, when the methylation level of the above CpG site is less than the standard value, it can be predicted that the subject has a low possibility that the medicinal therapy on the cancer is effective, and/or a high possibility that the medicinal therapy on the cancer is not effective.

The effective group and the ineffective group can be configured by properly defining a basis for effectiveness. For example, the effectiveness may be configured on the basis of pathological complete response (pCR) or good response. For details of the pathological complete response or good response, see Examples.

For example, a cutoff value appropriately configured to be able to distinguish the effective group from the ineffective group can be utilized as the above baseline. The cutoff value is a value that satisfies both high diagnostic sensitivity (specificity true positive rate) and high diagnostic specificity (specificity true negative rate) when a disease is determined using that value as a basis.

The diagnostic sensitivity (or simply sensitivity) is a ratio of subjects diagnosed properly among subjects having a particular status. When a "positive" result is obtained for all subjects having the particular status, the sensitivity is 100%.

The diagnostic specificity (or simply specificity) is a ratio of subjects properly diagnosed among subjects having no particular status. When a "negative" result is obtained for all subjects having no particular status, the specificity is 100%.

A method of calculating the cutoff value is well-known in the present field. For example, the methylation level of the above CpG site is analyzed in the effective group and the ineffective group, the diagnostic sensitivity and the diagnostic specificity in any methylation level are obtained in the effective group and the ineffective group, and an ROC (receiver operating characteristic) curve is made based on these values. Then, the methylation level which gives the maximum diagnostic sensitivity and diagnostic specificity is sought, and this value can be used as the cutoff value. A diagnostic efficiency (a ratio of the total number of true positive cases and true negative cases to the number of all cases) in any methylation level is sought, and the methylation level by which the highest diagnostic efficiency is calculated can also be used as the cutoff value. Alternatively, in the light of excluding as possible the case that a subject in which the medicinal therapy on the cancer is not actually effective is erroneously predicted as a subject in which the medicinal therapy on the cancer is effective (false-positive) (furthermore, delaying a timing to receive a surgical treatment to worsen a medical state), the diagnostic specificity may be more emphasized to determine the cutoff value.

The method of the present invention may further comprise measuring other markers associated with nature of the cancer in the cancer tissue sample. Examples of the other markers include the presence or absence or the change in dose of the expression of a certain gene, non-coding RNA or a protein, the presence or absence or the change in dose of a certain metabolite (e.g., modified protein such as phosphorylated protein), genetic polymorphism (e.g., SNP, haplotype), translocation, methylation of genomic DNA or their degree. In the method of the present invention, the diagnostic specificity can be enhanced by further measuring the other cancer marker. For example, it has been confirmed that in the case of breast cancer, if an estrogen receptor is negative in pathological diagnosis, the diagnostic specificity can be further enhanced (the Examples). Estrogen receptor herein refers to ERα unless otherwise described. A method of examining the presence or absence of the expression of estrogen receptor is not particularly limited, and a typically used enzyme antibody method (LSAB: labeled streptavidin biotinylated antibody) can be suitably used.

The present invention also provides a diagnostic kit for diagnosing an effect of the medicinal therapy on a cancer.

The diagnostic kit of the present invention comprises analytical means for analyzing the methylation of a cytosine residue in one or more CpG site present within the nucleotide sequence in the promoter region, the non-translation region or the translation region of HSD17B4 gene, more preferably in the CpG site normally present between positions 56 and 94 on the basis of the transcription start site, and still preferably in the CpG site present at positions 92 and 93 on the basis of the transcription start site of HSD17B4 gene. Such analytical means include one or two or more means selected from the group consisting of bisulfite, one or more primers, one or more nucleic acid probes, a restriction enzyme, an anti-methylated cytosine antibody, and a nanopore. The diagnostic kit of the present invention can be used for conducting the analytical method as described above.

Preferably, the diagnostic kit of the present invention comprises a combination of means for enabling a specific analysis of the CpG site described above and means for enabling an analysis of methylated cytosine (e.g., bisulfite, anti-methylated cytosine antibody, or methylation specific restriction enzyme). The means for enabling the specific analysis of the CpG site described above include, for example, one or more primers, one or more nucleic acid probes, a restriction enzyme, and a nanopore. One or more primers or one or more nucleic acid probes are preferred. The nucleic acid probe may be immobilized to the solid phase. The means for enabling the analysis of methylated cytosine include, for example, bisulfite, a primer for sequencing, an anti-methylated cytosine antibody, a methylation specific restriction enzyme, and an ICON probe method. Bisulfite or the anti-methylated cytosine antibody is preferred.

The diagnostic kit of the present invention may comprise auxiliary means in addition to the above analytical means. Such auxiliary means include, for example, deoxyribonucleoside triphosphate (dNTP), buffer, a stabilizing agent, an enzyme (e.g., DNA polymerase, sulfurylase, apyrase), a labeling substance, and a substrate for the enzyme.

When the diagnostic kit of the present invention comprises the anti-methylated cytosine antibody, it may further comprise a secondary antibody (e.g., anti-IgG antibody) and a detection reagent for the secondary antibody.

The diagnostic kit of the present invention may further comprise a device capable of collecting a biological sample. The device capable of collecting the biological sample is not particularly limited as long as the biological sample can be obtained from the subject, and includes, for example, a biopsy device such as a biopsy needle.

In the bisulfite pyrosequencing used in Example, (a) a pair of PCR primers and (b) a sequencing primer have been used as the means for enabling the specific analysis of the above CpG site, and (c) DNA polymerase, (d) sulfurylase, (e) luciferase and luciferin, (f) apyrase, (g) dNTP, and (h) bisulfite have been used as the means for enabling the analysis of methylated cytosine. Therefore, when the diagnostic kit of the present invention is used for the bisulfite pyrosequencing of the above CpG site, it may comprise, for example, constituent elements of (a) to (h) above.

The present invention also provides a medicinal therapy on a cancer.

The medicinal therapy of the present invention comprises:
(1) analyzing a methylation level of a cytosine residue in one or more CpG sites present within a nucleotide sequence in a promotor region, an untranslated region or a translated region of HSD17B4 gene in a cancer tissue sample taken from a human subject;
(2) predicting an effect of the medicinal therapy on the cancer based on the analyzed methylation level;
(3) selecting a human predicted to receive the effect of the medicinal therapy on the cancer; and
(4) giving the medicinal therapy to the selected human.

The items (1) and (2) in the medicinal therapy of the present invention can be performed in the same way as in (1) and (2) in the prediction method of the present invention.

The item (3) in the medicinal therapy of the present invention can be performed by selecting the human predicted to receive the effect of the medicinal therapy on the cancer based on the prediction in (2).

In (4) in the medicinal therapy of the present invention, the medicinal therapy is given to the selected human. The medicinal therapy is the treatment with the anticancer agent as described above. For example, when the cancer is the HER2-positive cancer, the medicinal therapy with the HER2 inhibitor is given. The treatment with the anticancer agent can be performed in a typical mode employed for that anticancer agent.

The present invention also provides a method of selecting a treatment on a cancer comprising:
(1) analyzing a methylation level of a cytosine residue in one or more CpG sites present within a nucleotide sequence in a promotor region, an untranslated region or a translated region of HSD17B4 gene in a sample taken from a human subject; and (2) selecting the treatment on the cancer based on the analyzed methylation level (1) in the selection method of the present invention can be performed in the same way as in (1) in the prediction method of the present invention.

The analysis of the methylation level in (2) in the selection method of the present invention can be performed in the same way as the analysis in (2) in the prediction method of the present invention. When no effect of the medicinal therapy with an existing anticancer agent (e.g., trastuzumab) is anticipated by the methylation level analyzed in (2), for example, the drug can be changed to the other anticancer agent, or the other anticancer agent can be combined. In addition, a pharmaceutical capable of suppressing or promoting the expression of HSD17B4 gene or a pharmaceutical capable of methylating, in particular, a non-coding region of HSD17B4 gene can be also combined. Further, the surgical therapy such as a radiation therapy can be also combined. As described above, the method of the present invention enables to select a more effective treatment method of a human being which is a therapeutic objective based on the methylation level analyzed in (2).

EXAMPLES

Hereinafter, the present invention will be described in more detail by Examples, but the present invention is not limited to these Examples.

1. Tissue Samples

Tissue samples were collected from 67 patients enrolled in a neoadjuvant clinical trial. All the samples for this study were obtained from patients who received weekly paclitaxel (80 mg/m² per week) and trastuzumab (a loading dose of 4 mg/kg followed by 2 mg/kg per week) for a total of 12 doses. The patients underwent mastectomy, and the response was pathologically assessed. The study protocol was approved by the National Cancer Center Ethics Committee, and was registered at the UMIN Clinical Trial Registry. All the patients were provided written informed consent.

Two specimens were obtained from a patient by core needle biopsy of a primary tumor before starting the neoadjuvant therapy, and fixed with two kinds of method. One specimen was fixed with neutral buffered formalin for microscopic examination using thin section stained with H&E, and the other was fixed with the PAXgene Tissue System (Qiagen, Germany) and embedded in low-melting paraffin for DNA/RNA extraction using 10 slices of sections with thickness of 10 μm. A certificated and experienced pathologist conducted microscopic examination of biopsy specimens to obtain the fraction of cancer cells to all the cells and to select specimens contained a sufficient number of tumor cells for molecular analyses. The pathologist also analyzed surgical specimens to determine the response.

In the present invention, pathological complete response (pCR) corresponds to Grade 3 in response determination criteria in Table 1 (cited from "General rules for clinical and pathological recording of breast cancer" edited by Japanese Breast Cancer Society, the 17th edition, page 84 (2012), Kanehara & Co., Ltd) and refers to the case in which no residual cancer cell is found in breast duct. Meanwhile, patients of Grade 2 or upper in Table 1 can be predicted to receive a highly effective neoadjuvant therapy even when they cannot be classified into pCR, and thus these patients are addressed as a "good response case" separately from pCR in this specification.

TABLE 1

| Grade 0, No response | | Almost no change in cancer cells by treatment is observed |
|---|---|---|
| Grade 1 slightly efficacious | 1a) Mild effect | Mild change of cancer cells is observed regardless of areas. Alternatively, high level change is observed in about less than ⅓ of cancer cells |
| | 1b) Moderate effect | High level change is observed in about ⅓ or more and less than ⅔ of cancer cells |
| Grade 2 Considerably efficacious | 2a) High level effect | High level change is observed in about ⅔ or more of cancer cells. But, clear focus is observed. |
| | 2b) Extremely high level effect | Effect significantly close to complete response (Grade 3) is observed, but tiny amount of cancer cells remains. |
| Grade 3 Complete response | | All cancer cells are in necrosis or disappear. Cancer tissue has been replaced with granuloma-like tissue or fibrotic focus. |

The 67 HER2-positive breast cancers were classified into 64 cases of invasive ductal carcinoma, 2 cases of invasive lobular carcinoma and 1 case of other histological type. For hormones, 34 cases (50.7%) were positive for estrogen receptor, and 26 cases (38.8%) were positive for progesterone receptor. Only samples with a tumor cell fraction (percentage of cancer cells in tissue sample) of 40% or more were used. Detailed Clinicopathological characteristics in the 67 cases of HER2-positive breast cancer patients are shown in Table 2.

TABLE 2

Clinicopathological characteristics of HER2-positive breast cancer patients.

| | pCR | | Non-pCR | |
|---|---|---|---|---|
| The number of patients | 22 | | 45 | |
| Clinical tumor stage (%) | | | | |
| cT1 | 1 | (4.6) | 3 | (6.7) |
| cT2 | 17 | (77.2) | 32 | (71.1) |
| cT3 | 3 | (13.6) | 8 | (17.8) |
| cT4 | 1 | (4.6) | 2 | (4.4) |
| Tumor size (cm) | 1.5-7.0 | | 0-10.0 | |
| Lymph node metastasis stage (%) | | | | |
| cN0 | 6 | (27.3) | 19 | (42.2) |
| cN1 | 12 | (54.5) | 21 | (46.7) |
| cN2 | 1 | (4.6) | 4 | (8.9) |
| cN3 | 3 | (13.6) | 1 | (2.2) |
| Clinical disease stage (%) | | | | |
| IIA | 7 | (31.8) | 20 | (44.4) |
| IIB | 9 | (40.9) | 13 | (28.9) |
| IIIA | 2 | (9.1) | 9 | (20.0) |
| IIIB | 1 | (4.6) | 2 | (4.4) |
| IIIC | 3 | (13.6) | 1 | (2.2) |
| Histological observation (%) | | | | |
| Invasive ductal carcinoma | 21 | (95.4) | 43 | (95.6) |
| Invasive lobular carcinoma | 0 | (0) | 2 | (4.4) |
| Others | 1 | (4.6) | 0 | (0) |
| Estrogen receptor (%) | | | | |
| Positive | 5 | (22.7) | 29 | (64.4) |
| Negative | 17 | (77.3) | 16 | (35.6) |

TABLE 2-continued

Clinicopathological characteristics of HER2-positive breast cancer patients.

|  | pCR |  | Non-pCR |  |
|---|---|---|---|---|
| Progesterone receptor (%) |  |  |  |  |
| Positive | 3 | (13.6) | 22 | (48.9) |
| Negative | 19 | (86.4) | 23 | (51.1) |
| Ki-67(%) | 26.5-80 |  | 10-96.5 |  |

2. Bisulfite Pyrosequencing of HSD17B4 Gene Region

Figure 1:
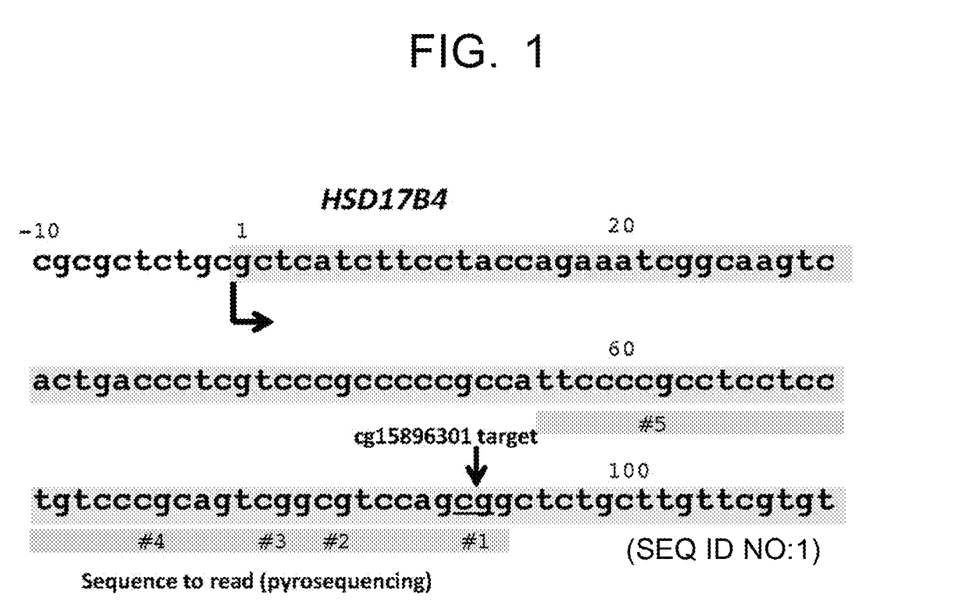
FIG. 1 shows the structure in the proximity of the transcription start site of HSD17B4 gene. Assigning "g" at the transcription start site as position 1, the nucleotide sequence consisting of the nucleotide residues from positions 56 to 94 and including five CpG sites (#1 to #5) was read by using pyrosequencing method.

A partial nucleotide sequence of HSD17B4 gene is shown in FIG. 1. The nucleotide sequence consisting of nucleotide residues at positions 56 to 94 including five CpG sites (#1 to #5) assigning "g" at the transcription start site as position 1 was read by pyrosequence. The methylation levels of five CpG sites were measured and calculated by the following procedures.

According to the method as previously described (T. Yoshida et al., Int. J. Cancer 128 (2011) pp. 33-39), sodium bisulfite modification was performed using 1 μg of genomic DNA. The modified DNA was suspended in 40 μl of Tris-EDTA buffer, and an aliquot of 2 μl was used for bisulfite pyrosequencing. The primers used for pyrosequencing were obtained from Qiagen (PyroMark CpG Assay). The PCR products labelled with biotin were annealed to 0.2 μM pyrosequencing primers, and pyrosequencing was carried out using the PSQ 96 Pyrosequencing System (Qiagen, Calif., USA). The methylation levels were calculated using PSQ Assay Design software (Qiagen).

The methylation level was calculated as a β value in the range of 0 (completely no methylation) to 1 (fully methylated), and this was expressed as a percent. The measured methylation level was corrected using the fraction of cancer cells in a sample. A specific correction formula is as follows. An upper limit of a normalized methylation level is determined to be 100. When a calculated value by the following formula exceeded 100, this was analyzed as "100% of normalized methylation level".

The normalized methylation level=100×(the measured methylation level (%))/(the fraction of cancer cells in the sample (%))].

The fraction of cancer cells (%) was obtained by microscopic examination.

3. Statistical Analysis

The Fisher's exact test was used to calculate the significant difference in relative frequency between two groups. Significant differences in the normalized methylation levels between the responders and non-responders were evaluated by the Mann-Whitney U test. In the univariate analysis, the odds ratios (ORs) and 95% confidence interval (95% CI) were calculated. The multivariate logistic regression analyses were also performed to detect the factors independently associated with the apparent likelihood of the response to the combined trastuzumab and chemotherapy after excluding confounders. All statistical analyses were conducted by PASW statistics version 18.0.0 (SPSS Japan Inc.).

4. Results

Figure 2:
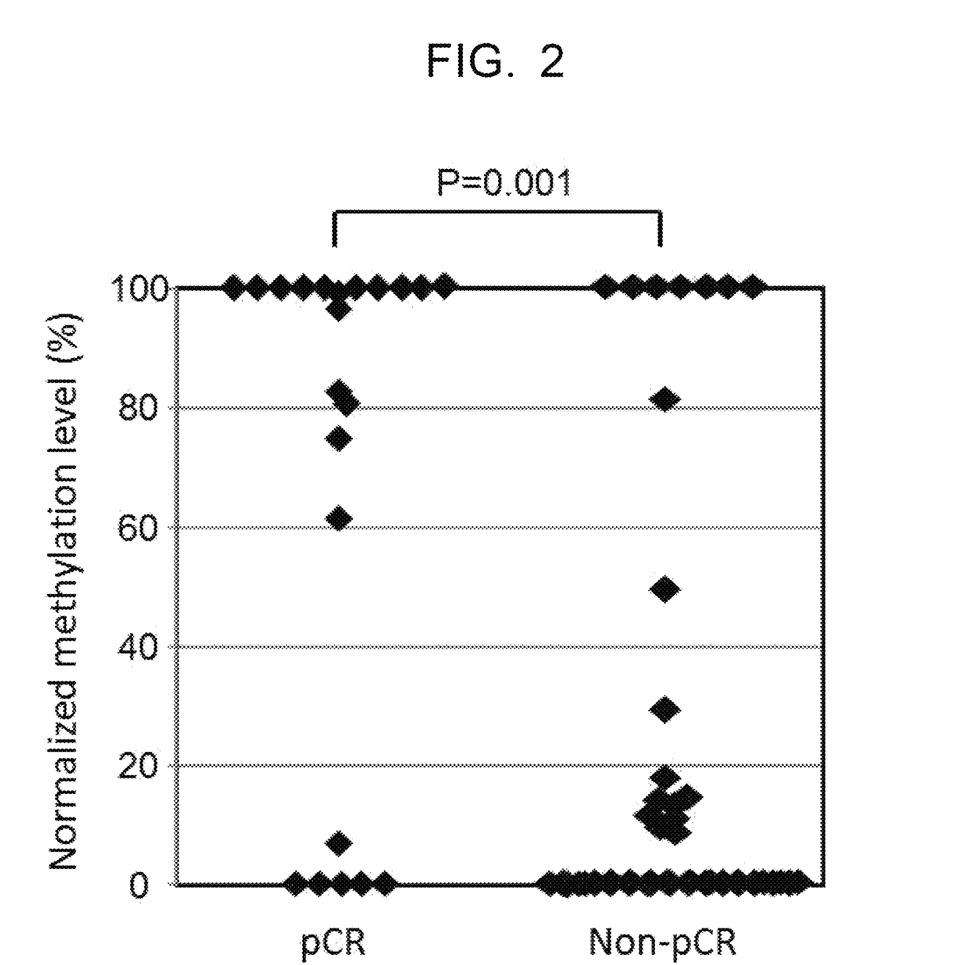
FIG. 2 shows methylation levels of CpG site #1 of HSD17B4 gene in 22 cases of pathologically complete response (pCR) and 45 cases of non-pCR.
Figure 3:
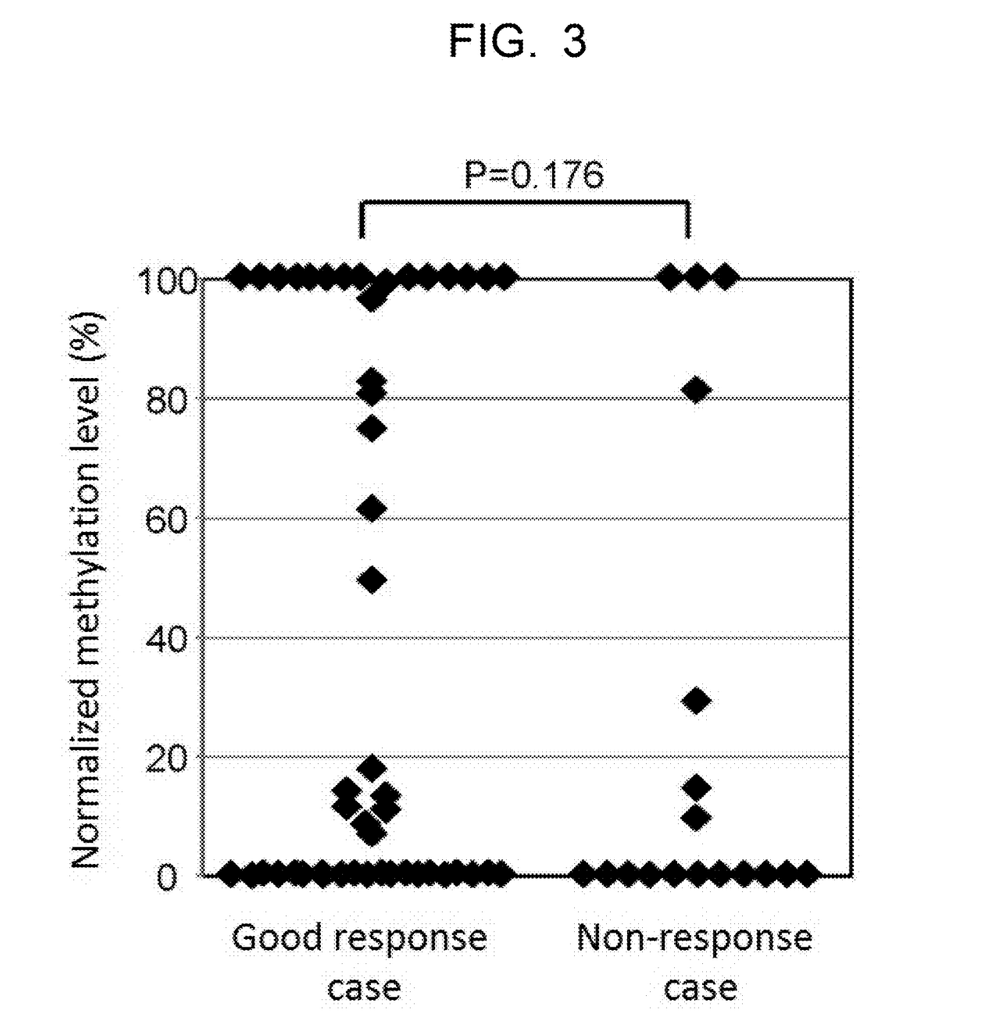
FIG. 3 shows methylation levels of CpG site #1 of HSD17B4 gene in 49 cases with good response and 18 cases with non-response.

The normalized methylation level of the CpG site of #1 in FIG. 1, an average value of the normalized methylation levels of the CpG sites of #1 to #5 in pCR group and other case group, and significant difference (P value) between two group are shown in Table 3. It was found that both the normalized methylation level of the CpG site of #1 and the average value of the normalized methylation levels of #1 to #5 were significantly became higher in the pCR group. Particularly, as shown in FIG. 2, it was found that the normalized methylation level of the CpG site of #1 was much higher in the pCR group than the other case group (p=0.001). On the other hand, even in the CpG site of #1, the normalized methylation level in the good response group (G2a or higher) was not said to be significantly higher than that in the non-response group (p=0.176, FIG. 3).

TABLE 3

Normalized methylation level in respective CpG sites.

| CpG site | Normalized methylation level average (%) | | P value* (pCR group vs Non-pCR group) |
|---|---|---|---|
|  | pCR group | Non-pCR group |  |
| #1 | 68.2 | 21.3 | 0.001 |
| Average of #1 to #5 | 53.8 | 23.4 | 0.008 |

*calculated by Mann-Whitney U test

Hereinafter, the "methylation of HSD17B4 gene" indicates the methylation of the CpG site of #1 in HSD17B4 gene unless otherwise described. A cutoff of the methylation level of HSD17B4 gene was configured to be 50%, a value of 50% or higher was determined to be "positive", and a value lower than 50% was determined to be "negative". Clinical diagnosis results when pCR was determined to be positive and the other cases were determined to be negative are shown in Table 4. Likewise, clinical diagnosis results when the good response case was determined to be positive and the non-response case was determined to be negative are shown in Table 5. The sensitivity was 77.2% and the specificity was 84.4% in the clinical diagnosis results of the methylation level when pCR was determined to be positive. On the other hand, the sensitivity was 40.8% and the specificity was 77.8% in the clinical diagnosis results of the methylation level when the good response case was determined to be positive.

TABLE 4

Clinical diagnosis results (positive: pCR; negative: other cases)

|  |  | pCR | | |
|---|---|---|---|---|
|  |  | Positive | Negative | Total |
| Methylation level | Positive | 17 | 7 | 24 |
|  | Negative | 5 | 38 | 43 |
| Total |  | 22 | 45 | 67 |

Sensitivity: 77.2%
Specificity: 84.4%
Positive predictive value: 70.8%

TABLE 5

Clinical diagnosis results (positive: good response case; negative: non-response case)

|  |  | Good response case | | |
|---|---|---|---|---|
|  |  | Positive | Negative | 計 |
| Methylation level | Positive | 20 | 4 | 24 |
|  | Negative | 29 | 14 | 43 |
|  | Total | 49 | 18 | 67 |

Sensitivity: 40.8%
Specificity: 77.8%
Positive predictive value: 83.3%

Results of the clinicopathological characteristics of the 67 cases compiled by dividing into a positive group and a negative group of the methylation level of HSD17B4 gene are shown in Table 6. Among the multiple clinical factors shown in Table 6, the determination of positive/negative for the hormone receptors, particularly estrogen receptor exhibited highly significant difference between the positive group and the negative group of the methylation level, and suggested to have high association with the methylation level. A multivariate analysis including clinical tumor stage (cT), lymph node metastasis stage (cN), clinical disease stage (cStage), estrogen receptor (ER), progesterone receptor (PgR), and Ki-67 labelling index showed that HSD17B4 methylation was an independent predictive factor for the response to HER2-directed therapy (Table 7).

TABLE 6

Association between HSD17B4 gene methylation and clinicopathological characteristics

|  | Methylation positive | Methylation negative | P value* |
|---|---|---|---|
| No. of patients | 24 | 43 |  |
| Clinical tumor stage (%) |  |  |  |
| cT1 | 1 | 3 | 0.76 |
| cT2 | 19 | 30 |  |
| cT3 | 3 | 8 |  |
| cT4 | 1 | 2 |  |
| Lymph node metastasis stage |  |  |  |
| cN0 | 9 | 16 | 1 |
| cN1 | 12 | 21 |  |
| cN2 | 1 | 4 |  |
| cN3 | 2 | 2 |  |
| Clinical disease stage |  |  |  |
| IIA | 9 | 18 | 1 |
| IIB | 9 | 13 |  |
| IIIA | 3 | 8 |  |
| IIIB | 1 | 2 |  |
| IIIC | 2 | 2 |  |
| Histological observation |  |  |  |
| Invasive ductal carcinoma | 23 | 41 | 1 |
| Others | 1 | 2 |  |
| Estrogen receptor |  |  |  |
| Positive | 7 | 26 | 0.02 |
| Negative | 17 | 17 |  |
| Progesterone receptor |  |  |  |
| Positive | 5 | 20 | 0.07 |
| Negative | 19 | 23 |  |

TABLE 6-continued

Association between HSD17B4 gene methylation and clinicopathological characteristics

|  | Methylation positive | Methylation negative | P value* |
|---|---|---|---|
| Ki-67(%) |  |  |  |
| 50≥ | 15 | 18 | 0.13 |
| 50< | 9 | 25 |  |
| pCR |  |  |  |
| Positive | 16 | 6 | 2.20E−05 |
| Negative | 8 | 37 |  |

*P value was calculated by the Fisher's exact test.

TABLE 7

Determination of independent factors associated with response to HER2-directed therapy by multivariate logistic regression analysis

| Factors | The number of cases | Odd ratio | (95% CI) | | P value |
|---|---|---|---|---|---|
| HSD17B4 gene (methylated vs unmethylated) | 24/43 | 10.02 | 2.54 | 39.50 | 0.001 |
| cT (cT3 + cT4 vs cT1 + cT2) | 14/53 | 0.55 | 0.03 | 9.32 | 0.68 |
| cN (cN1 + cN2 + cN3 vs cN0) | 42/25 | 1.79 | 0.38 | 8.48 | 0.46 |
| cStage (III vs IV) | 18/49 | 1.28 | 0.09 | 18.61 | 0.86 |
| ER (negative vs positive) | 34/33 | 6.65 | 0.75 | 59.32 | 0.09 |
| PgR (negative vs positive) | 42/25 | 0.84 | 0.07 | 9.61 | 0.89 |
| Ki67 index (<50 vs ≥50) | 34/33 | 0.46 | 0.11 | 1.92 | 0.28 |

For the purpose of enhancing accuracy of prediction (specificity) of the response to the HER2-directed therapy, clinical evaluation was performed by combining the methylation level of HSD17B4 gene with the results of estrogen receptor. An examination of estrogen receptor is conducted for almost all of cases of patients with breast cancer by known methods, and the examination was performed for the 67 cases in the present Example as well. Clinical diagnosis results when the case in which the methylation level of HSD17B4 gene was positive and estrogen receptor was negative was determined to be "positive" and the other cases were determined to be "negative" as well as pCR was determined to be positive and the others were determined to be negative are shown in Table 8. Likewise, the clinical diagnosis results when the good response case was determined to be positive and the non-response case was determined to be negative are shown in Table 9. The clinical diagnosis results in combination of the methylation level and estrogen receptor when pCR was determined to be positive exhibited the sensitivity of 59.1% and the specificity of 91.1%. On the other hand, the clinical diagnosis results in combination of the methylation level and estrogen receptor when the good response case was determined to be positive exhibited the sensitivity of 32.7% and the specificity of 94.4%. One case determined to be "positive" in Table 9 was a case in which a tumor size was very large and the surgical operation was strongly recommended with or without the effect of the neoadjuvant therapy.

TABLE 8

Clinical diagnosis results (positive: pCR; negative: other cases)

|  |  | pCR | | |
| --- | --- | --- | --- | --- |
|  |  | Positive | Negative | Total |
| Methylation level (+)/ | Positive | 13 | 4 | 17 |
| ER* (−) | Negative | 9 | 41 | 50 |
|  | Total | 22 | 45 | 67 |

*ER: estrogen receptor
Sensitivity: 59.1%
Specificity: 91.1%
Positive indicative value: 76.5%

TABLE 9

Clinical diagnosis results (positive: good response case; negative: non-response case)

|  |  | Good response case | | |
| --- | --- | --- | --- | --- |
|  |  | Positive | Negative | Total |
| Methylation level (+)/ | Positive | 16 | 1 | 17 |
| ER* (−) | Negative | 33 | 17 | 50 |
|  | Total | 49 | 18 | 67 |

*ER: estrogen receptor
Sensitivity: 32.7%
Specificity: 94.4%
Positive indicative value: 94.1%

The invention claimed is:

1. A method of treating a HER2-positive breast cancer in a human subject, comprising:
measuring the methylation level of a cytosine residue in one or more CpG sites present within a nucleotide sequence in an untranslated region of HSD 17B4 gene, wherein the untranslated region consists of SEQ ID NO:1, in a breast cancer cell-containing sample taken from a human subject suffering from the HER2-positive breast cancer;
predicting an effect of a treatment with a trastuzumab on the HER2-positive breast cancer based on the measured methylation level, wherein increased methylation level of the cytosine residue in the one or more CpG sites indicates that the trastuzumab is effective for the treatment;
selecting a human subject with high methylation level of the cytosine residue in the one or more CpG sites; and treating the selected human subject with the trastuzumab.

2. A method of selecting a treatment with a trastuzumab on a HER2-positive breast cancer, comprising:
measuring a methylation level of a cytosine residue in one or more CpG sites present within a nucleotide sequence in an untranslated region of HSD 17B4 gene, wherein the untranslated region consists of SEQ ID NO:1, in a breast cancer cell-containing sample taken from a human subject suffering from the HER2-positive breast cancer; and
selecting the trastuzumab as the treatment for the HER2-positive breast cancer based on the measured methylation level, wherein increased methylation level of the cytosine residue in the one or more CpG sites compared to a control population in which said treatment is ineffective, indicates that the trastuzumab is effective for the treatment, and treating the human subject with the trastuzumab, wherein the measuring comprises measuring with at least one means selected from the group consisting of bisulfite, primers, a nucleic acid probe, a restriction enzyme, an anti-methylated cytosine antibody, and a nanopore.

3. The method of claim 1, comprising:
measuring a methylation level of a cytosine residue in one or more CpG sites present within a nucleotide sequence in an untranslated region of HSD 17B4 gene, wherein the untranslated region consists of SEQ ID NO:1, in a breast cancer cell-containing sample taken from a human subject suffering from the HER2-positive breast cancer;
predicting an effect of a treatment with a trastuzumab in combination with another anticancer agent on the HER2-positive breast cancer based on the measured methylation level, wherein increased methylation level of the cytosine residue in the one or more CpG sites indicates that the trastuzumab in combination with another anticancer agent is effective for the treatment;
selecting a human subject with high methylation level of the cytosine residue in the one or more CpG sites; and
treating the selected human subject with the trastuzumab in combination with another anticancer agent.

4. The method of claim 1, wherein the sample is at least one sample selected from the group consisting of a blood, a body fluid, a breast cancer tissue, and a breast cancer cell.

5. The method of claim 1, wherein the CpG site is a CpG site normally present between positions 56 and 94 from the transcription start site at position 11 of SEQ ID NO: 1.

6. The method of claim 1, wherein the CpG site is a CpG site normally present at positions 92 and 93 from the transcription start site at position 11 of SEQ ID NO: 1.

7. The method of claim 1, further comprising measuring the expression of estrogen receptor in the breast cancer cell-containing sample.

8. The method of claim 1, wherein the measuring comprises measuring with at least one means selected from the group consisting of bisulfite, primers, a nucleic acid probe, a restriction enzyme, an anti-methylated cytosine antibody, and a nanopore.

9. The method of claim 1, wherein the measuring is performed by a bisulfite sequencing method, a bisulfite pyrosequencing method, a methylation specific PCR method, a restriction enzyme landmark genome scanning (RLGS) method, a single nucleotide primer extension (SNuPE) method, a CpG island microarray method, a MethyLight method, a COBRA method, a mass spectroscopy (mass array) method, use of a methylation specific restriction enzyme, a high resolution melting analysis (HRM) method, a nanopore analysis method, an ICON probe method, a methylation specific MLPA method, or an immunoassay.

* * * * *

SEQUENCE LISTING

<160> NUMBER OF SEQ ID NOS: 2

<210> SEQ ID NO 1
<211> LENGTH: 120
<212> TYPE: DNA
<213> ORGANISM: Homo sapiens
<220> FEATURE:
<221> NAME/KEY: CpG_site
<222> LOCATION: (102)..(103)
<223> OTHER INFORMATION: cg15896301 target site of HSD17B4

<400> SEQUENCE: 1

```
cgcgctctgc gctcatcttc ctaccagaaa tcggcaagtc actgaccctc gtcccgcccc      60
cgccattccc cgcctcctcc tgtcccgcag tcggcgtcca gcggctctgc ttgttcgtgt     120
```

<210> SEQ ID NO 2
<211> LENGTH: 2001
<212> TYPE: DNA
<213> ORGANISM: Homo sapiens
<220> FEATURE:
<221> NAME/KEY: CpG_site
<222> LOCATION: (1092)..(1093)
<223> OTHER INFORMATION: cg15896301 target site of HSD17B4

<400> SEQUENCE: 2

```
tttgggaact gataaatgtc cgtgaaatct tcacaattta tgttcctctg ctgcggctct      60
agcaggtccc tctgtttggg gtccatgact tcccgcaaca tccaatcaat cctccataat     120
gggcaaagtg atctttccat agtgtaaatg tgttcccacc actctctgga gtaatcctac     180
ttaaaaccgt tttcagcaca aaattcaaac atctaaacat gatcttgctg gctttgcttt     240
tgtggcttta ccctctttct ccccaaacct agctagtgtt tgtgctgcct gtaatgccct     300
tctttctttg caggggtcgc cactttaggt cctggtcctc cttcagaaag ttttcctct     360 ttctccccag cggggatagg gtctgtttat tttgacacca ttagctcact tacacacatt     420
ggtcacaagt ctaggctgca ccgttattga aagtttacca tctgactctg agtagcttga     480
ggatcctatc aaaactcagg agatgctcag taaatgttga ttgaactatg actgttctca     540
acatacaaac gcaagatcat ttaggaacac ttgtcaaaat gttttttgccc cttgagattc     600 tattttggga ggtaagcagt gggggtccag gactctgcat tttgacagtc ccctgatgtt     660
tgcatgtaga agtgcaggga ttattacact gacaaatctt taccatccct aaggggggact     720 ttccttccca ggggctatct ctggaagccc ctcaaggata ggggccgcat gctgtttctc     780
taggtcagca actaaaccca gaaaacgttt attgagtgaa tgatgaaacg acaggtgaat     840
```

-continued

```
agatgaacgc aaggtgtcga gttaactatt cttctacaca agtcctagca gctcccattg    900
cttccagccg cagaaatggc ccctggaagg caagtcttcc agcgagtgga gtcactctta    960
actacatttc ccaggattcc aagggagccg cgcgctctgc gctcatcttc ctaccagaaa   1020
tcggcaagtc actgaccctc gtcccgcccc cgccattccc cgcctcctcc tgtcccgcag   1080
tcggcgtcca gcggctctgc ttgttcgtgt gtgtgtcgtt gcaggcctta ttcatgggct   1140
caccgctgag gttcgacggg cgggtggtac tggtcaccgg cgcggggggca ggtgagcatg   1200 cgaaggttgg aggccgcgcc ccttgctgag gcgcagctgg ctgctctttt cgggccggca   1260
tacgcgcgca gccgcagctg aggtcacccc gctgaggtgg tggggagggg aatggttatt   1320
cttgaggcac cgcatctctt gaggaggaaa gagccggaaa cacctggtct ctcaagcagg   1380
tacagcccgc ttctccccag cacccccggtg tgggcttccc aaggtcctgc ctgagaggag   1440
aggccaggct gggctgctga ttgcaaaact gggtgaaagt tctccctgac ccttatctgt   1500
gggcatcgat tgttactctt cctgcaatta actctcttag atctttgcct agtcttttaa   1560
aggactgaaa agccgcgagg ggcgggggct ggaattcgcc ccctgaagcg cagagatgtc   1620
agctcctgaa aagtcattcg gtcgttcagt gtttgtttcc ctctgtcgta agattttaag   1680
ttcgtgagag gaccttcttt aaagagggcg tctgataaga gcccttcccc gttggagttt   1740
gtatgcttag caagtcacaa tctgttctcg aaatccactg gagtcttggc agaggttgta   1800
agctcaaatg cgcacagggg tcaggcgtat gatggagaaa gaaaatggga gtaggatggg   1860
cacatctgag gaactggaga gcagagaatt ccgaagtgga ccggccagtg ggaaagttgc   1920
ctgtatttca ggagcggcaa aatggaaaat tgttatgtga aatagcccca ttttttaaag   1980
tacaaaaaat taaaacaaac c                                              2001
```